United States Patent
Coszach et al.

(10) Patent No.: US 8,614,338 B2
(45) Date of Patent: Dec. 24, 2013

(54) METHOD FOR STEREOSPECIFICALLY RECYCLING A PLA POLYMER MIXTURE

(75) Inventors: Philippe Coszach, Courcelles (BE); Jonathan Willocq, Saint-Sauveur (BE)

(73) Assignee: Futerro S. A., Escanaffles (BE)

( * ) Notice: Subject to any disclaimer, the term of this patent is extended or adjusted under 35 U.S.C. 154(b) by 0 days.

(21) Appl. No.: 13/389,592

(22) PCT Filed: Jul. 19, 2010

(86) PCT No.: PCT/EP2010/060426
§ 371 (c)(1),
(2), (4) Date: Feb. 8, 2012

(87) PCT Pub. No.: WO2011/029648
PCT Pub. Date: Mar. 17, 2011

(65) Prior Publication Data
US 2012/0165554 A1   Jun. 28, 2012

(30) Foreign Application Priority Data
Sep. 10, 2009   (BE) .................................. 2009/0554

(51) Int. Cl.
*C07D 319/00*   (2006.01)
(52) U.S. Cl.
USPC .......................................................... 549/274

(58) Field of Classification Search
USPC ............................................................ 549/274
See application file for complete search history.

(56) References Cited

U.S. PATENT DOCUMENTS

| | | | |
|---|---|---|---|
| 5,136,057 A | 8/1992 | Bhatia | |
| 8,431,683 B2 * | 4/2013 | Coszach et al. | ............... 528/480 |

FOREIGN PATENT DOCUMENTS

| | | | |
|---|---|---|---|
| EP | 0628533 | * 6/1993 | .............. C07C 51/09 |
| EP | 0628533 A1 | 12/1994 | |
| WO | 92/00974 A | 1/1992 | |

OTHER PUBLICATIONS

PCT International Search Report issued in connection with PCT/EP2010/060426 issued Aug. 27, 2010.

* cited by examiner

*Primary Examiner* — Nizal Chandrakumar
(74) *Attorney, Agent, or Firm* — Reichel IP LLP; Kevin Erdman; Mark Reichel

(57) ABSTRACT

The present invention relates to a method for the stereospecific chemical recycling of a mixture of polymers based on polylactic acid PLA, in order to reform the monomer thereof or one of the derivatives thereof. The latter may enter the traditional lactate market or once again serve as a raw material for synthesizing PLA.

16 Claims, No Drawings

METHOD FOR STEREOSPECIFICALLY RECYCLING A PLA POLYMER MIXTURE

CROSS-REFERENCE TO RELATED APPLICATIONS

This application is the U.S. national phase of PCT/EP2010/060426, filed Jul. 19, 2010. PCT/EP2010/060426 claims the benefit under the Paris Convention of Belgian Patent Application No. 2009/0554, filed on Sep. 10, 2009, the disclosures of which are explicitly incorporated by reference herein.

FIELD OF THE INVENTION

The present invention relates to a method for the stereospecific chemical recycling of a mixture of PLA-based polymers, in order to reform the monomer thereof or one of the derivatives thereof. The latter may form part of the traditional market of lactates or once again serve as a raw material for the synthesis of PLA.

At the present time, in order to promote the growth in biopolymers, the use of which is compatible with respect for the environment, it is essential to be able to demonstrate the viability of the management of the end of life of these products. The objective of the present invention is to respond to this problem in the case of polylactic acid (PLA) by proposing an original solution distinguishing itself from those already existing through its stereospecific character.

PRIOR ART

The management of the end of life of plastics materials is a very important element in the viability of a plastic on the market (for example, PVC has been withdrawn from the plastic bottle market failing an effective recycling system). Just like plastics of non-renewable origin (coming from petrochemistry) and although their end of life channels are more numerous, biopolymers are confronted with technical challenges when it is a question of this end of life management. In particular when very large volumes are spoken of, generated in convenience markets. This is why it is important to deal with this problem.

At the present time, various methods making it possible to manage the end of life of waste are already known such as dumping, incineration, composting or mechanical recycling. These various end of life techniques are not ideal since the plastics materials are not recycled as base elements (monomers) that are therefore directly and perpetually usable. Despite everything, these methods are viable for PLA but only if the flow of material is composed solely of PLA. This is because, if other polymers contaminate the PLA, the various aforementioned techniques are made difficult. For example, in the case of contamination with PET, the latter is not degraded in a compost. In the case of contamination with PVC, incineration is possible but involves the use of expensive filters because of harmful emissions. With regard to mechanical recycling, the product obtained is completely adulterated if it is composed of a mixture of polymers.

Chemical recycling is often cited as the ideal recycling method. It consists of transforming the polymer by means of a chemical process such as for example: thermal or catalytic hydrocarbon cracking, pyrolysis that gives the monomers again, etc. A chemical recycling system for PET is known, which consists of depolymerisation thereof by means of a diol, also referred to as glycolysis. The molecular chain is broken and the products obtained are terephthalic acid and ethylene glycol. Nevertheless, some degradation mechanisms during this depolymerisation cause irreversible structural modifications of the material, modifications that may be responsible for difficulties during successive transformations.

A system for the chemical recycling of PLA may also be envisaged in order to recover the monomer, the lactic acid or one of the derivatives thereof. Some patents for example claim a hydrolysis (Brake L. D., Subramanian N. S., U.S. Pat. No. 5,229,528, 1993; Galactic, BE Patent 56,491, 2009) or a solvolysis (Brake L. D., U.S. Pat. No. 5,264,614, 1993; Brake L. D., U.S. Pat. No. 5,264,617, 1993; Galactic, BE Patent 56,493, 2009) of polyhydroxy acid including the PLA with the production of hydroxy acids or esters thereof. Thermal degradations (pyrolysis for example) of PLA are also known, leading to the formation of lactide (F. D. Kopinke, M. Remmler, K. Mackenzie, M. Moder, O. Wachsen, Polymer Degradation and Stability, 53, 329-342, 1996) by means of a cyclisation mechanism by addition-elimination. However, these methods have a low monomer yield. In addition these various techniques are often performed at high temperature and/or high pressure, which causes chemical and optical degradation of the lactic acid obtained.

It is well known that there exist two optically active forms of lactic acid: L-lactic acid (L-LA) and D-lactic acid (D-LA). Consequently, the lactide, a cyclic dimer of lactic acid, may be in three diastereoisomeric forms depending on whether they consist of two D-lactic acid molecules: D-lactide, two L-lactic acid molecules: L-lactide, or one L-lactic acid molecule and one D-lactic acid molecule: meso-lactide. Meso-lactide is characterised by a melting point of around 50° C. whereas the melting points of L- and D-lactide isomers is 97° C.

A problem common to all these methods is that none is stereospecific. This is because they do not make it possible to eliminate the D enantiomers that may be generated firstly by the whole of the PLA production process and secondly by the various chemical recycling processes. This means that D enantiomers are formed when working with an L-type PLA (the form mainly present on the market). Identically, there will be the formation of L enantiomers when working with type D PLA.

This progressive enrichment in undesired enantiomer with regard to the lactic acid or derivatives thereof will have a significant impact on the yield and the costs of production of a new PLA.

There therefore exists a requirement for a method for the stereospecific recycling of PLA that is simple, effective and non-adulterating in order to reform its monomer or one of its derivatives. The latter may enter the traditional lactate market or once again serve as a raw material for the synthesis of PLA.

For the purpose of simplification, the invention will be presented in the remainder of the present document starting from an L-type PLA (the majority of the constituent elements of type L), knowing that it may just as well be suitable for starting with a type D PLA (the majority of the constitutive elements of type D).

BRIEF DESCRIPTION OF THE INVENTION

The subject matter of the present invention is a method for the chemical stereospecific recycling of a mixture of polymers necessarily containing PLA, lactide or one of the derivatives thereof, which may either be hydrolysed into lactic acid or one of the derivatives thereof, or be used as a monomer or comonomer for synthesising PLA or PLA copolymers.

This method for the chemical stereospecific recycling of a mixture of polymers containing PLA is characterised in that it comprises a. putting the mixture of polymers in solution in a lactic ester able to dissolve the PLA fraction;

b. depolymerisation by transesterification of the PLA fraction coming from the previous step, this depolymerisation being stopped when the mixture of oligoesters coming from the depolymerisation reaches a number average molecular weight of between 400 and 5000 amu.

One embodiment of the present invention is that, between steps a and b, there may be a step of separating the lactic ester and PLA dissolved on the one hand and the mixture of insoluble polymers on the other hand.

Another embodiment of the present invention consists of subjecting the mixture of oligoesters of step b to a catalytic cyclisation step with the production of a vapour phase rich in lactide and a liquid phase rich in oligoesters.

Another embodiment of the present invention consists of grinding and/or compacting the mixture of polymers, prior to the putting in suspension, until a weight/volume ratio of between 0.005 and 1.4 $t/m^3$ is obtained.

Another embodiment of the present invention consists of separating the residual lactic ester from the oligoesters before beginning the cyclisation step.

Another object of the invention is to propose a simpler and more economical method of producing PLA. This is because, unlike the conventional methods starting from lactic acid or one of the derivatives thereof, where thorough purification is carried out with regard to the production of both lactic acid and lactide, in the context of the present invention, the purification is carried out on a single occasion concerning the production of lactide.

Another subject matter of the present invention is the isomeric purification of the flow of PLA treated by chemical recycling and intended for producing a new PLA. This is because the global process of producing PLA and, to a much lesser extent, the reaction of forming oligoesters described above gives rise to a certain racemisation of the PLA, which signifies the appearance of type D enantiomers when working with type L PLA (the form mainly present on the market). Through the stereospecific purification of lactide in the context of the present invention, we obtain a lessening of undesired enantiomer unlike the existing recycling methods.

DETAILED DESCRIPTION OF THE INVENTION

The method of the invention comprises a step of putting the mixture of polymers in suspension in a lactic ester able to dissolve the PLA fraction followed by a separation firstly of the lactic ester, the PLA and other dissolved impurities and secondly the mixture of other polymers and impurities that are insoluble. The solution containing the PLA thus obtained is then subjected to a catalytic depolymerisation reaction by transesterification in order to form oligoesters. The depolymerisation reaction by transesterification is then stopped at a given moment and the residual lactic ester separated.

The oligoester thus obtained then undergoes a cyclisation reaction in order to produce lactide that will finally be purified stereospecifically so as to obtain a fraction of purified lactide having a meso-lactide content of between 0.1% and 40%.

In the context of the present invention, the raw materials used during this chemical recycling may come from off-specification products in the production units, production scrap in the transformation units and end of life end products. A grinding of the mixture of polymers containing PLA can be carried out by various techniques, such as for example grinding by shearing, by impact, dry or under water. The objective of this step being to increase the specific surface of the materials, so as to obtain a weight/volume ratio of between 0.05 and 1.4 $t/m^3$, which facilitates the handling steps and accelerates the following dissolution step, making the method more easily carried out on an industrial scale. In the context of the invention, one or more grinding steps can be envisaged, the number thereof depending on the starting product but also the cost of these operations and final granulation sought. It is also possible to pre- or post-treat these flows of mixtures of polymers containing PLA in particular by proceeding with a washing with water or other solution such as for example a soda, potash, detergent solution etc. Other treatments, such as manual sorting or automatic separation (magnetic for example) may be envisaged, all this for the purpose of eliminating any waste that might impair the quality of the end product or to complicate the purification thereof. It is also obvious that, if the polymer mixture waste containing PLA to be processed has a suitable specific surface for starting the putting in solution, this grinding step can be omitted without departing from the method of the present invention.

Simultaneously, or following this grinding step, when it is performed, a step of densification or compacting can be envisaged in order to compact the material, which would improve the handling and logistics steps.

The mixture of polymers containing PLA, ground or not and compacted or not, is then put in solution in lactic ester before the step of depolymerisation by transesterification. It is a case of esters such as methyl lactate, ethyl lactate, propyl lactate, butyl lactate, hexyl lactate, etc, and more generally a lactic acid alkyl ester the alkyl radical of which has 1 to 12 carbon atoms.

The putting in solution can also be carried out without prior grinding if the form of the mixture of polymers containing PLA (weight/volume ratio) so permits. This is because one of the problems of the processing of this type of flow is the difference in specific weight of the various materials to be processed, even after the grinding step. This putting in solution is fairly rapid and can be carried out in a few minutes.

This dissolution may be prior to or simultaneous with the following step and carried out at different temperatures ranging up to the melting point of PLA. The applicant company has also shown that it was possible to eliminate the water present in the PLA during this step of putting in solution. This is because, having regard to the boiling point of the lactic acid esters recommended in the method of the present invention, putting in solution can be carried out at a temperature of more than 100° C. and at atmospheric pressure and water can easily be eliminated by condensation.

In the case of contamination of the flow of PLA by another polymer (PET, PE, PVC, PP, PC or any other usual polymer), it is possible to eliminate the latter, for example by filtration, if necessary hot. This is because lactic esters do not enable the aforementioned polymers to be put in solution for the required processing times. This separation can be carried before or after the following step.

The applicant company has shown that the partial depolymerisation of PLA, in a PLA/lactic ester ratio by weight of between 0.5 and 3, could be carried out by depolymerisation by transesterification at a temperature of between 80° et 180° C., preferentially between 110° and 160° C. and more preferentially between 120° and the boiling point of lactic ester, under a negative pressure or a pressure lying between atmospheric pressure and 10 bar or even more. This step of depolymerisation by transesterification of PLA enables oligoesters to be produced by reaction of an ester bond of the PLA and an alcohol function. Surprisingly, the applicant company found that this alcohol function could come either from an added alcohol or from the lactic ester that was used during the putting in solution. In the context of this invention, the following can be used apart from the lactic esters mentioned previously: alcohols containing 1 to 12 carbon atoms, such as methanol, ethanol, n-butanol, isobutanol, sec-butanol, tert-butanol, n-propanol, isopropanol, 2-ethylhexanol, 2-ethylbutanol, hexanol, etc.

The use of a transesterification catalyst is necessary in order to move the equilibrium of the reaction towards the formation of the oligoester, this catalyst may be solid or liquid and of the Lewis acid type such as for example tin octoate, tin lactate, antimony octoate, zinc octoate, PTSA (para-toluene sulfonic acid), etc, or preferentially basic, in the guanidine family, such as for example TBD (triazabicyclodecene) and derivatives thereof.

A particular embodiment of this invention is the putting in solution in the lactic ester during which the moisture potentially present in the PLA is eliminated by evaporation. The release of lactic acid and the oligomerisation catalysed by this same molecule are thus avoided Likewise, when the depolymerisation by transesterification reaction is carried out in the presence of a basic catalyst, the absence of water in the medium avoids any problem relating to acidity during this step and subsequent steps of the method.

When the required molecular weight is reached, between 400 and 5000 amu (measured by GPC with PS calibration), preferably between 400 and 3000 amu, a quality that avoids firstly the problems relating to the transfer of highly viscous products and secondly an excessive residual acidity (in the case of the presence of water) in the product obtained at the end of the depolymerisation step, the depolymerisation by transesterification reaction is stopped. The reaction can be stopped by eliminating the alcohol function (coming from the lactic ester or the alcohol) which makes it possible to keep control of the molecular weight of the oligoester. In this context, any technology allowing rapid extraction of the alcohol or lactic ester will be favoured, such as for example thin film technology. The depolymerisation may also be stopped by neutralisation of the catalyst, which makes it possible to be less dependent on the time factor. Another possibility consists of an early stoppage of the reaction knowing that it would continue just a little during a slower treatment of elimination of the residual lactic ester such as for example batch distillation. One of the favoured options of the present invention will consist of eliminating the alcohol or the ester, which does not exclude the possibility of maintaining it in the medium and passing directly to the cyclisation step.

Once formed, it is preferable that the oligoester be directly treated, especially if the transesterification catalyst has not been deactivated. This step consists of the catalytic and thermal cyclisation of the oligoester, preferably with the lactic ester removed, in order to produce a vapour phase rich in lactide. The use of a catalyst is essential in order to reduce the thermocracking temperature and thus to prevent chemical and optical deterioration of the lactide synthesised. The catalyst will be solid or liquid and of the Lewis acid type such as for example tin octoate, tin lactate, antimony octoate, zinc octoate, PTSA (paratoluene sulfonic acid), etc, or preferentially basic, in the guanidine family, such as for example TBD (triazabicyclodecene) and derivates thereof. Ideally, it will be identical to that used in the depolymerisation by transesterification step.

The reactor will preferably be selected so as to hold the mixture (oligoesters/catalyst) for as little as possible (from 0 to 30 minutes and preferentially from 0 to 15 minutes) at the reaction temperature while offering a large exchange surface and extraction volume. The working temperature will be sufficient to initiate the reaction, but not too high in order to avoid degradation or racemisation of the lactide: the temperature will be between 180° and 280° C. The optimum temperature will depend on the nature of the starting oligoesters (the molecular weight ranging from 400 to 5000 amu), and the nature of the catalyst and the pressure in the system.

Given the chemical instability of the lactide at the working temperatures and in order to move the equilibrium of the reaction towards the formation of the lactide, it is important for it to be extracted as quickly as possible from the reaction medium. In this context, it is preferable to keep the reaction medium under gaseous flow and/or under vacuum. The second option will be preferred since it also makes it possible to reduce the reaction temperature.

Following the various constraints announced above and without limiting the scope of the present invention, the use of an evaporator of the thin layer type appears to be particularly indicated. This is because, from this type of equipment, a liquid residue is extracted at the bottom, composed of the oligoesters with high molecular weights. At the top, the vapour phase rich in lactide is directly extracted and selectively condensed at a condenser fixed at a well determined temperature. This is because the temperature is maintained at a temperature such that firstly the volatile compounds such as water, ester and alcohol remain in the vapour phase (whereas the lactide and the heavy compounds are condensed), and not too low on the other hand so as to prevent crystallisation of the lactide. According to the nature and purity of the product harvested (raw lactide), this temperature will be between 70° and 125° C. It is also possible to work at a lower temperature and thus to crystallise the lactide, which will require the use of a condenser of the scraped surface type.

Given that the starting material consists of oligoesters, the crude material issuing from this selective condensation will be more stable over time, since it is less reactive, than a crude material that would be generated starting from lactic acid. In addition, this crude material will have a lower viscosity, which will increase the efficacy of certain purification technologies.

The subsequent step of the method consists of a purification of the crude material that makes it possible to control the meso-lactide content in the final lactide, this content having to be between 0.1% and 40%, preferably between 0.1% and 20%, which makes it possible to control and therefore prevent the enrichment in D enantiomer in the whole of the process.

In the context of the invention, various types of purification can be envisaged, such as for example crystallisation in a molten medium, meso-lactide having a melting point quite different from that of L-lactide, whether that be in a layer (Sulzer type) or in suspension (NIRO type), distillation with control of the meso-lactide content by acting on the number of theoretical plates and on the reflux level, solvent crystallisation, aqueous extraction (meso-lactide being more sensitive to hydrolysis than L-lactide), or in a solvent (different solubility and crystallisation temperature of meso-lactide compared with L-lactide). Any other technique for fulfilling the conditions stated above is also valid in the context of the invention.

The lactide thus obtained will have high purity and variability controlled according to the field of application for which it will be intended.

This is because, if it is intended for the synthesis of homo- or copolymers of PLA, its residual acidity and residual water content will for example by very low, namely respectively less than 10 meq/kg with regard to the residual acidity content and less than 100 ppm or even 50 ppm with regard to the residual water content.

The meso-lactide content for its part will be variable according to the characteristics required for the polymer (more crystalline or amorphous).

On the other hand, if it is intended to be used as a reaction intermediate or hydrolysed into lactic acid or one of its derivatives in the context of applications of an industrial type, the acidity, residual water or even meso-lactide content will be less critical.

Other details and particularities of the invention, given below by way of non-limitative examples, emerge from the description as a few possible forms of embodiment thereof.

Example 1

1.00 kg of PLA (at 99.5% L(+)) is put in solution in 666 g of ethyl lactate. The putting in solution is carried out in a two liter flask at atmospheric pressure and a temperature of 140° under stirring. When all the PLA has been put in solution, 1 g of TBD is added. The depolymerisation by transesterification reaction is continued for 24 hours at a temperature of 120° C. under reflux. The number average molecular weight being 1800 amu (measured by GPC). The ethyl lactate is then eliminated on a thin film (130° C., 100 millibars). 1088 g of oligoesters at 98.9% L(+) is then recovered.

The cyclisation reaction is then carried out at 250° C. and a pressure between 10 and 20 millibars, adding 2% of tin octoate to the mixture of oligoesters.

The vapour generated (impure lactide—crude material) is condensed and the crude material obtained purified by melt crystallisation.

The raw lactide (768 g) obtained is introduced into a crystalliser consisting of a vertical stainless steel tube. The double jacket of the tube is supplied with heat-transfer fluid by a thermostatically controlled heating unit in order to control the crystallisation, sweating and remelt phases. This raw material is melted at 102° C. Then the crystallisation is initiated on the wall by a progressive reduction in the temperature. Part of the raw material is crystallised on the walls, whereas the central part contains the liquid phase (drain) containing the majority of impurities. When the temperature reaches 60° C., the liquid phase is extracted by gravity and nitrogen blowing. The crystals are also covered with a film of impurities that the sweating step is to eliminate, the surface of the tube will from then on be very progressively heated so as to melt the surface of the crystals of lesser purity. The product is finally brought to its melting point in order to liquefy it and harvest it by gravity.

Three successive crystallisation stages were implemented and the characteristics of the end product are set out in table 1.

TABLE 1

Characteristics of the end product (lactide)

| Water[a] (%) | Lactic acid[b] (%) | Meso-LD[c] (%) | L-LD[c] (%) |
|---|---|---|---|
| 0.09 | 0.09 | 0.25 | 99.56 |

[a]determined by Karl Fischer measurement
[b]determined by volumetric analysis
[c]determined by GC Example 2

1.00 kg of PLA (at 95.3% L(+)) is put in solution in 666 g of ethyl lactate. The putting in solution was carried out in a 2 liter flask at atmospheric pressure and a temperature of 140° C. under stifling. When all the PLA has been put in solution, 319 g of anhydrous ethanol and 1 g of tin octoate are added. The depolymerisation by transesterification reaction is continued for 30 hours at a temperature of 120° C. and in a reactor that can work under pressure. The ethyl lactate and ethanol are then eliminated on a thin film (130° C., 100 millibars). An oligoester at 93.2% L(+) is thus recovered.

The cyclisation reaction is carried out at 250° C. and a pressure of between 10 and 20 millibars, adding 2% of tin octoate to the oligoester mixture.

The vapour generated (impure lactide—crude material) is condensed and a fraction of crude material obtained purified by solvent extraction.

The raw lactide (100 g) obtained is heated at 85° C. and mixed with 100 g of IPE (isopropyl ether) under stirring until homogenised. The suspension is then progressively cooled to −18° C. The crystals are then filtered and washed with IPE. The extraction operation was repeated on two and then three occasions and the lactide obtained was finally dried under vacuum on a rotary evaporator.

The characteristics of the end product are set out in table 2.

TABLE 2

Characteristics of the end product (lactide)

| Number of extractions | Water[a] (%) | Lactic acid[b] (%) | Meso-LD[c] (%) | L-LD[c] (%) |
|---|---|---|---|---|
| 2 | 0.012 | 0.12 | 3.7 | 96.2 |
| 3 | 0.012 | 0.1 | 1.3 | 98.5 |

[a]determined by Karl Fischer measurement
[b]determined by volumetric analysis
[c]determined by GC Example 3

A small quantity (10 g) of the lactide produced in example 1 is introduced into a test tube under nitrogen scavenging. After melting of the product (100° C.), 6 mg of tin octoate was added (so as to comply with a product/catalyst molar ratio of 4500). Once the solution is homogenised, it is immersed in an oil bath the temperature of which is thermostatically controlled at 180° C. After one hour of synthesis, the polymer is recovered. This polymer was analysed by GPC in chloroform at 35° C.: its weighted molecular weight distribution by weight is 98000 (Mw with PS calibration).

Example 4

Out of the lactide produced in example 1, 100 g is introduced into a flask. In order to obtain a 90% concentrated lactic acid, 38.8 g of demineralised water is added. The solution is then heated at 100° C. for 3 hours.

The characteristics of the final lactic acid are set out in table 3.

TABLE 3

Characteristics of the lactic acid

| Stereospecific purity[a] (%) | Concentration[b] (%) | FC colouring[c] (Hz) | HS colouring[d] (Hz) | Cation-metal content[e] |
|---|---|---|---|---|
| 99.8 | 90.5 | 8 | 20 | 23 ppm |

[a] determined by enzymatic analysis
[b] determined by volumetric analysis
[c] Fresh Colour determined by colorimetry
[d] Heat Stability determined by colorimetry after 2 hours heating at reflux
[e] determined by spectrometry

Example 5

800 g of PLA (at 95.5% L(+)) is put in solution in 533 g of ethyl lactate. The putting in solution was carried out in a 2 liter reactor making it possible to work under pressure and at a temperature of 140° C. under stirring (this operation was carried out at atmospheric pressure). When all the PLA was put in solution, 51 g of ethanol and 0.8 g of TBD are added. The depolymerisation by transesterification reaction is continued for 24 hours at a temperature of 140° C. The number average molecular weight being 1800 amu (measured by GPC). The ethyl lactate and ethanol are then eliminated on a thin film (140° C., 100 millibars). 1060 g of oligoesters at 95.2% L(+) are thus recovered.

An identical procedure to that described in example 1 was followed and, at the end of the three crystallisation stages, the product the characteristics of which are set out in table 4 below was obtained.

TABLE 4

Characteristics of the end product (lactide)

| Water[a] (%) | Lactic acid[b] (%) | Meso-LD[c] (%) | L-LD[c] (%) |
|---|---|---|---|
| 0.032 | 0.024 | 0 | 99.89 |

[a] determined by Karl Fischer measurement
[b] determined by volumetric analysis
[c] determined by GC

The invention claimed is:

1. Method for chemical stereospecific recycling of a mixture of polymers containing polylactic acid (PLA), the method comprises the steps of:
   a. combining the mixture of polymers and a lactic acid alkyl ester into a solution, wherein the lactic acid alkyl ester is capable of dissolving in the PLA fraction;
   b. depolymerizing the dissolved PLA fraction of step (a) by catalytic transesterification of said fraction at a temperature comprised between 80 and 180° C. and at a pressure comprised between a negative pressure or a pressure lying between atmospheric pressure and 10 bar;
   c. controlling the catalytic transesterification reaction by GPC to measure the molecular weight of the oligoesters formed during step (b);
   d. stopping the catalytic transesterification reaction when the molecular weight measured in step (c) of the oligoesters reaches a value comprised between about 400 and about 5000 amu;
   e. separating the residual lactic acid alkyl ester from the oligoester mixture;
   f. subjecting the oligoester mixture obtained in step (b) to a catalytic and thermal cyclisation step to form a vapor phase rich in lactide and a liquid phase rich in oligoester; and
   g. subjecting the raw lactide of step (f) to a stereospecific purification to recover a purified lactide fraction, the meso-lactide fraction of which is comprised between about 0.1% wt and 40% wt.

2. Method according to claim 1, wherein between steps (a) and (b), the method comprises a step of separating the lactic ester and the dissolved PLA from the mixture of insoluble polymers.

3. Method according to claim 1, wherein the mixture of polymers has weight/volume ratio comprised between 0.005 and 1.4 t/m3 prior to combining with the lactic acid alkyl ester.

4. Method according to claim 1, wherein the alkyl radical of the lactic acid alkyl ester comprised from 1 to 12 carbon atoms.

5. Method according to claim 4, wherein the lactic acid alkyl ester is ethyl lactate.

6. Method according to claim 1, wherein the catalytic transesterification reaction is operated at a temperature comprised between 110 and 160° C., preferably between 120° C. and the boiling point of the lactic acid alkyl ester, and at a pressure between atmospheric pressure and 10 bar.

7. Method according to claim 1, wherein the stopping step (d) is achieved either by eliminating the alcohol function or by neutralization of the catalyst.

8. Method according to claim 1, wherein the weight ratio PLA/lactic alkyl ester in step (a) is between about 0.5 to 3.

9. Method according to claim 1, wherein the partial depolymerization by transesterification of step (b) is achieved by reaction between the dissolved PLA and an alcohol function selected from an added alcohol or preferably from the lactic acid alkyl ester.

10. Method according to claim 1, wherein the catalyst used for transesterification reaction in step (b) is identical to the catalyst used for the cyclisation of step (f).

11. Method according to claim 1, wherein the purification of the raw lactide obtained in step (f) is achieved by means of a stereospecific method selected from the group consisting of crystallization in a molten medium in a layer, crystallization in a molten medium in suspension, crystallization in a solvent medium, distillation and aqueous extraction.

12. Method according to claim 1, wherein the purification of the raw lactide obtained in step (f) is achieved by crystallization.

13. Method according to claim 1, wherein the purification by crystallization is achieved in at least three separate stages.

14. A purified lactide formed by the method according to claim 1, wherein the purified lactide comprises at least 95% of L-lactide isomer.

15. A purified lactide according to claim 14, wherein the purified lactide comprises at least 98% of L-lactide isomer.

16. A purified lactide according to claim 15, wherein the purified lactide comprises at least 99% of L-lactide isomer.

* * * * *